United States Patent
Shimada et al.

(10) Patent No.: US 9,439,598 B2
(45) Date of Patent: Sep. 13, 2016

(54) MAPPING AND ABLATION OF NERVES WITHIN ARTERIES AND TISSUES

(71) Applicant: Neuro Ablation, Inc., Minneapolis, MN (US)

(72) Inventors: Jin Shimada, Grantsburg, WI (US); Gregory G. Brucker, Minnetonka, MN (US); William J. Rissmann, Deephaven, MN (US)

(73) Assignee: NeuroMedic, Inc., Minneapolis, MN (US)

( * ) Notice: Subject to any disclaimer, the term of this patent is extended or adjusted under 35 U.S.C. 154(b) by 630 days.

(21) Appl. No.: 13/796,944

(22) Filed: Mar. 12, 2013

(65) Prior Publication Data

US 2013/0274614 A1 Oct. 17, 2013

Related U.S. Application Data

(60) Provisional application No. 61/623,220, filed on Apr. 12, 2012, provisional application No. 61/677,244, filed on Jul. 30, 2012.

(51) Int. Cl.
*A61B 5/00* (2006.01)
*A61B 5/026* (2006.01)
*A61B 18/14* (2006.01)
(Continued)

(52) U.S. Cl.
CPC ........... *A61B 5/4836* (2013.01); *A61B 5/0205* (2013.01); *A61B 5/026* (2013.01); *A61B 5/04001* (2013.01); *A61B 5/1076* (2013.01); *A61B 18/1492* (2013.01); *A61B 18/1815* (2013.01); *A61B 18/24* (2013.01); *A61B 18/02* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01);
(Continued)

(58) Field of Classification Search
CPC .............. A61B 18/02; A61B 18/1492; A61B 18/1815; A61B 18/24; A61B 2018/00404; A61B 2018/00434; A61B 2018/00511; A61B 2018/00577; A61B 2018/00642; A61B 2018/00839; A61B 2018/1861; A61B 5/0205
USPC ......................................................... 606/12
See application file for complete search history.

(56) References Cited

U.S. PATENT DOCUMENTS

| 4,573,481 A | 3/1986 | Bullara |
| 5,048,034 A | 9/1991 | Tulip |

(Continued)

*Primary Examiner* — Lynsey Crandall
*Assistant Examiner* — Joshua Rosefelt
(74) *Attorney, Agent, or Firm* — Fredrickson & Byron, P.A.

(57) ABSTRACT

Method and systems for ablating nerves including measurement of physiological parameters and/or electrical conduction. The method may include ablating nerves within an artery of a patient such as the renal artery and may include advancing a catheter into the artery, measuring a physiological parameter, emitting an electrical pulse into a wall of the artery, measuring the physiological parameter during or after the step of emitting the electrical pulse, ablating the artery wall, then repeating the steps of measuring the physiological parameter, emitting an electrical pulse, and measuring the physiological parameter during or after the step of emitting the electrical pulse. The change in the physiological parameter caused by the electrical pulse before ablation may be compared to the change in the physiological parameter caused by the electrical pulse after ablation to determine the degree of nerve ablation achieved and whether or not to perform further ablation.

13 Claims, 10 Drawing Sheets

(51) Int. Cl.
*A61B 18/24* (2006.01)
*A61B 18/18* (2006.01)
*A61B 5/04* (2006.01)
*A61B 5/107* (2006.01)
*A61B 5/0205* (2006.01)
*A61B 18/02* (2006.01)
*A61N 7/02* (2006.01)
*A61B 18/00* (2006.01)

(52) U.S. Cl.
CPC ........... *A61B 2018/00839* (2013.01); *A61B 2018/1861* (2013.01); *A61N 7/022* (2013.01)

(56) References Cited

U.S. PATENT DOCUMENTS

| | | | |
|---|---|---|---|
| 5,178,161 A | 1/1993 | Kovacs | |
| 5,303,703 A | 4/1994 | Monti-Bloch | |
| 5,718,241 A * | 2/1998 | Ben-Haim | A61B 5/06 600/515 |
| 5,775,331 A | 7/1998 | Raymond et al. | |
| 5,897,505 A | 4/1999 | Feinberg et al. | |
| 6,292,695 B1 | 9/2001 | Webster, Jr. et al. | |
| 6,466,817 B1 | 10/2002 | Kaula et al. | |
| 6,500,128 B2 | 12/2002 | Marino | |
| 6,564,078 B1 | 5/2003 | Marino et al. | |
| 6,692,490 B1 | 2/2004 | Edwards | |
| 6,760,616 B2 | 7/2004 | Hoey et al. | |
| RE38,705 E | 2/2005 | Hill et al. | |
| 6,912,419 B2 | 6/2005 | Hill et al. | |
| 6,973,346 B2 | 12/2005 | Hafer et al. | |
| 7,079,883 B2 | 7/2006 | Marino et al. | |
| 7,162,303 B2 | 1/2007 | Levin et al. | |
| 7,177,677 B2 | 2/2007 | Kaula et al. | |
| 7,238,179 B2 | 7/2007 | Brucker et al. | |
| 7,238,180 B2 | 7/2007 | Mester et al. | |
| 7,267,674 B2 | 9/2007 | Brucker et al. | |
| 7,349,743 B2 | 3/2008 | Tadlock | |
| 7,470,236 B1 | 12/2008 | Kelleher et al. | |
| 7,505,848 B2 | 3/2009 | Flann et al. | |
| 7,522,953 B2 | 4/2009 | Kaula et al. | |
| 7,553,307 B2 | 6/2009 | Bleich et al. | |
| 7,578,819 B2 | 8/2009 | Bleich et al. | |
| 7,610,005 B2 | 10/2009 | Ide | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,738,968 B2 | 6/2010 | Bleich | |
| 7,738,969 B2 | 6/2010 | Bleich | |
| 7,769,438 B2 | 8/2010 | Hartlep et al. | |
| 7,865,236 B2 | 1/2011 | Cory et al. | |
| 7,949,409 B2 | 5/2011 | Bly et al. | |
| 7,959,577 B2 | 6/2011 | Schmitz et al. | |
| 8,027,716 B2 | 9/2011 | Gharib et al. | |
| 8,050,769 B2 | 11/2011 | Gharib et al. | |
| 8,055,349 B2 | 11/2011 | Gharib et al. | |
| 8,068,912 B2 | 11/2011 | Kaula et al. | |
| 8,090,436 B2 | 1/2012 | Hoey et al. | |
| 2004/0122482 A1 | 6/2004 | Tung et al. | |
| 2005/0288730 A1 * | 12/2005 | Deem et al. | 607/42 |
| 2006/0041277 A1 | 2/2006 | Deem et al. | |
| 2006/0200219 A1 | 9/2006 | Thrope et al. | |
| 2006/0265014 A1 | 11/2006 | Demarais et al. | |
| 2006/0276852 A1 | 12/2006 | Demarais et al. | |
| 2007/0129760 A1 | 6/2007 | Demarais et al. | |
| 2007/0167913 A1 | 7/2007 | Elkins et al. | |
| 2007/0173899 A1 | 7/2007 | Levin et al. | |
| 2007/0265687 A1 | 11/2007 | Deem et al. | |
| 2008/0051859 A1 | 2/2008 | Sharkey et al. | |
| 2008/0058757 A1 | 3/2008 | Pajunk et al. | |
| 2008/0140180 A1 | 6/2008 | Dolan et al. | |
| 2008/0255642 A1 | 10/2008 | Zarins et al. | |
| 2009/0240106 A1 | 9/2009 | Solanki | |
| 2009/0276023 A1 | 11/2009 | Morris et al. | |
| 2009/0299214 A1 | 12/2009 | Wu et al. | |
| 2009/0299447 A1 * | 12/2009 | Jensen et al. | 607/130 |
| 2010/0042185 A1 | 2/2010 | Curtis | |
| 2010/0137952 A1 | 6/2010 | Demarais et al. | |
| 2010/0168731 A1 | 7/2010 | Wu et al. | |
| 2010/0168739 A1 | 7/2010 | Wu et al. | |
| 2010/0174282 A1 | 7/2010 | Demarais et al. | |
| 2010/0222854 A1 | 9/2010 | Demarais et al. | |
| 2010/0249643 A1 | 9/2010 | Gozani et al. | |
| 2011/0004207 A1 | 1/2011 | Wallace et al. | |
| 2011/0060324 A1 | 3/2011 | Wu et al. | |
| 2011/0166563 A1 | 7/2011 | Cheng et al. | |
| 2011/0207758 A1 | 8/2011 | Sobotka et al. | |
| 2011/0208173 A1 | 8/2011 | Sobotka et al. | |
| 2011/0208175 A1 | 8/2011 | Sobotka et al. | |
| 2011/0257564 A1 | 10/2011 | Demarais et al. | |
| 2011/0257641 A1 | 10/2011 | Hastings et al. | |
| 2011/0264075 A1 | 10/2011 | Leung et al. | |
| 2011/0264086 A1 | 10/2011 | Ingle | |
| 2011/0264116 A1 | 10/2011 | Kocur et al. | |
| 2011/0306851 A1 | 12/2011 | Wang | |
| 2012/0029500 A1 | 2/2012 | Jenson | |
| 2012/0029505 A1 | 2/2012 | Jenson | |
| 2012/0029509 A1 | 2/2012 | Smith | |
| 2012/0029510 A1 | 2/2012 | Haverkost | |
| 2012/0029511 A1 | 2/2012 | Smith et al. | |
| 2012/0029512 A1 | 2/2012 | Willard et al. | |
| 2012/0029513 A1 | 2/2012 | Smith et al. | |
| 2012/0116382 A1 * | 5/2012 | Ku et al. | 606/33 |
| 2012/0191079 A1 * | 7/2012 | Moll | A61B 5/0084 606/14 |

* cited by examiner

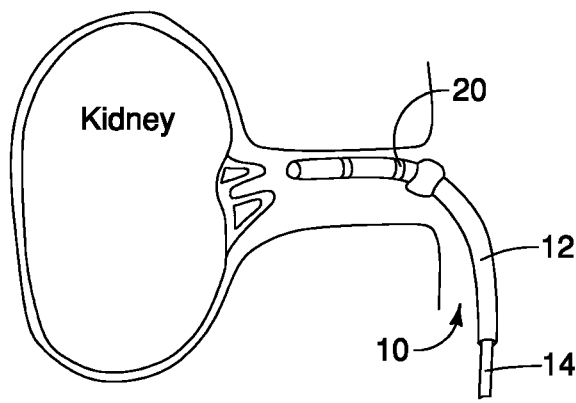
FIG. 3
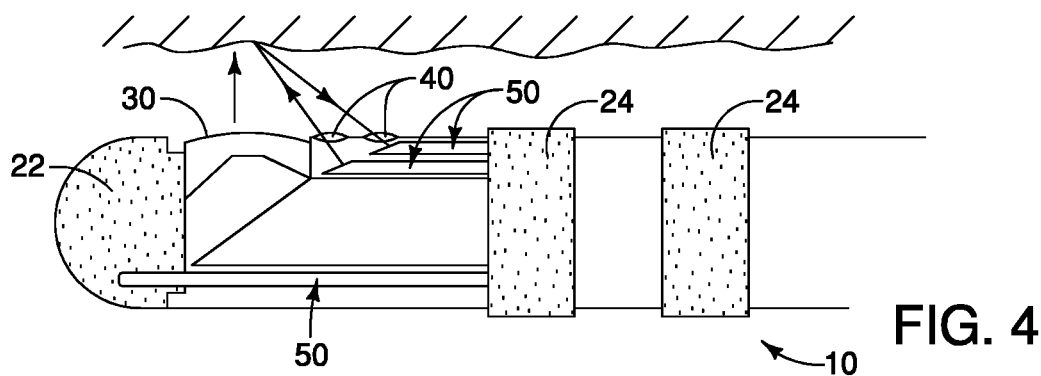
FIG. 4
FIG. 5
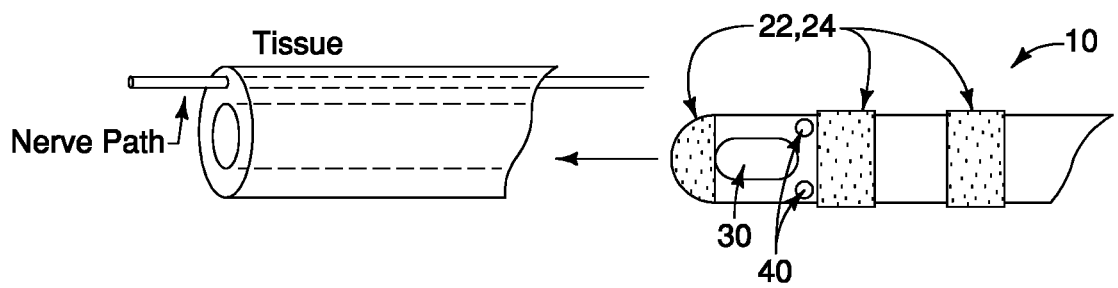

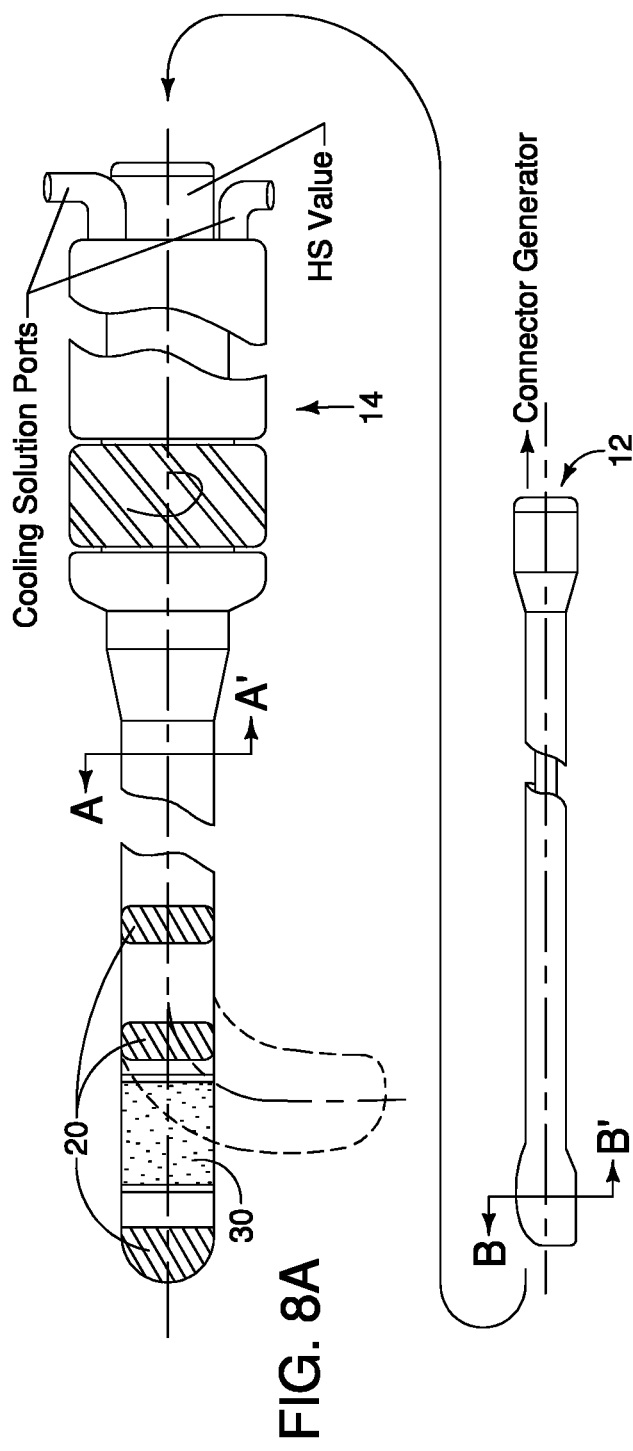
FIG. 8A
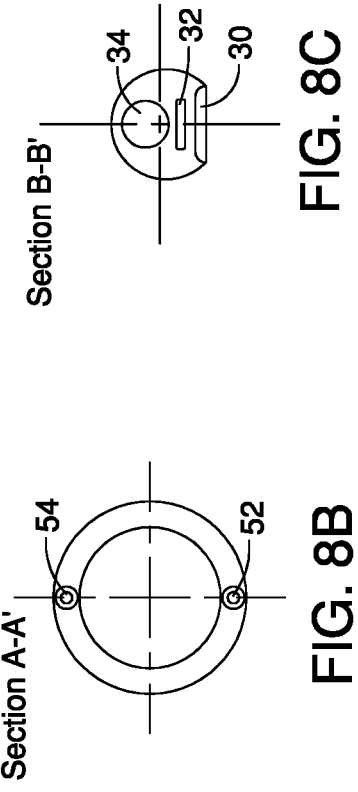
FIG. 8B
FIG. 8C

MAPPING AND ABLATION OF NERVES WITHIN ARTERIES AND TISSUES

PRIORITY

This application claims priority to U.S. provisional patent application No. 61/623,220 filed Apr. 12, 2012 and U.S. provisional patent application No. 61/677,244 filed Jul. 30, 2012, the disclosures of which are hereby incorporated by reference.

BACKGROUND

Hypertension is a common disease which can have serious adverse consequences, including an increased risk of stroke, damage to organs including the heart, kidneys, brain, blood vessels and retinas. However, while hypertension is serious and numerous medications exist which attempt to control hypertension, in many cases it remains difficult to manage. For many patients, medications only partially reduce blood pressure and the patients remain at risk.

The difficulty in controlling blood pressure may be due to the complex nature of blood pressure maintenance by the body. Blood pressure is affected by multiple interrelated factors including cardiac activity, the degree of vasoconstriction/vasodilation, the degree of sympathetic stimulation, kidney function, salt and water consumption and balance, the amount of renin/angiotensin produced by the kidneys, and the presence of any abnormalities of the sympathetic nervous system, as well as possibly other unknown factors.

The kidneys play a key role in blood pressure regulation. Sympathetic nerve stimulation to the kidneys results in the production of renin, retention of sodium and water, and changes in renal blood velocity, all of which lead to increased blood pressure. Through a system of interactions with other organs, the production of renin ultimately leads to the production of aldosterone, which causes the conservation of sodium, the secretion of potassium, increased water retention and increased blood pressure. An interruption of the renin-angiotensin-aldosterone system is, therefore, one method of reducing hypertension. For example, therapeutic agents such as angiotensin converting enzyme (ACE) inhibitors, angiotensin receptor blockers (ARBs), and renin inhibitors reduce blood pressure by affecting this system. More recently, attempts have been made to reduce renin production and, therefore, reduce blood pressure by surgically transecting the sympathetic nerves to the kidneys to prevent sympathetic stimulation of the kidneys.

Recent studies have successfully reduced blood pressure in hypertensive patients through the use of ablation of the sympathetic nerves within the renal arteries. The ablation is performed through a catheter and radiofrequency (RF) energy is applied to the interior of the arteries in linear arcs that extend circumferentially around the artery. A single arc may extend around the entire artery or a series of arcs may be created. The arcs in the series of arcs may be spaced apart longitudinally somewhat but are overlapping radially such that the entire inner circumference is ablated by a line of ablation at some point along the length of the artery. In either case, the result is that the ablated arcs transect all nerves running through the walls of the renal arteries. By encircling the arteries with lines of ablation, the surgeon is sure to transect the renal nerves, even though the actual locations of the nerves are unknown.

Because renal artery ablation surgeries have only been performed relatively recently, the long term effectiveness and the risk of long term side effects from such surgeries is unknown. Due to the vital nature of the kidneys and the necessity of maintaining adequate blood velocity to these organs, the risk that such surgeries could lead to scarring and stenosis of the renal arteries is an important consideration. If significant stenosis were to occur, the result could be a loss of kidney function, which could be more problematic than the initial hypertension. A more refined approach to renal nerve ablation is, therefore, desirable.

SUMMARY

Embodiments of the invention include devices and methods for mapping and ablating nerves, such as mapping and ablating the nerves within the renal arteries, though the same or similar devices and methods may alternatively be used in other locations, as well.

Various embodiments include methods of ablating nerves within an artery of a patient. In some embodiments, the method includes advancing a catheter including a first stimulation electrode and an ablation element into the artery to a first location, then measuring a physiological parameter, then emitting an electrical pulse from the first stimulation electrode into a wall of the artery at the first location and measuring the physiological parameter during or after the step of emitting an electrical pulse. The next steps may include ablating the artery wall at the first location, and then measuring the physiological parameter of the patient at the first location, emitting an electrical pulse from the first electrode at the first location, and then measuring the physiological parameter. In some embodiments, the physiological parameter is blood velocity in the artery or artery diameter at the first location. In some embodiments, the catheter also includes a blood velocity sensor. The electrical pulse may be the same when performed both before and after ablation, such as having an equal amplitude and duration. In some embodiments, the artery is the renal artery.

In some embodiments, the method also includes calculating a first change in the physiological parameter as a difference between a measurement of the physiological parameter obtained before and after stimulation before ablation, and calculating a second change in the physiological parameter as a difference between a measurement of the physiological parameter obtained before and after stimulation after ablation. The method may also include calculating a difference between the first change in the physiological parameter and the second change in the physiological parameter. In some embodiments, if the difference between the first change in the physiological parameter and the second change in the physiological parameter is insufficient to indicate a desired amount of ablation, the method may include ablating the artery wall at the first location again.

In some embodiments, the method also includes the steps of repositioning the catheter within the artery at a second location, then emitting an electrical pulse from the first electrode at the second location, then measuring the physiological parameter at the second location, and then ablating the artery wall at the second location. The method may further include measuring the physiological parameter at the second location between steps after repositioning the catheter at the second location and before emitting the electrical pulse at the second location.

In some embodiments, the catheter includes a second stimulation electrode and the method further includes the steps of emitting an electrical pulse from the second stimulation electrode at a second location in the artery, then measuring the physiological parameter at the second location, then ablating the artery wall at the second location.

In some embodiments, the method is a method of ablating a nerve within a renal artery of a patient. The method may include advancing a catheter including a stimulation electrode and an ablation element into the artery. The stimulation electrode and the ablation element may be one element or may be separate elements. The method may further include positioning the stimulation electrode against a wall of the artery at a first location, then measuring blood velocity in the artery at the first location, then emitting an electrical pulse from the first electrode, then measuring blood velocity in the artery at the second location during or after emitting the electrical pulse, then ablating the artery wall at the first location after step, then measuring the blood velocity, emitting an electrical pulse, and measuring blood velocity again. If the difference between the first change in blood velocity and the second change in blood velocity is insufficient to indicate a desired amount of ablation, the method may further include ablating the artery wall at the first location a second time. The change in the physiological parameter includes the difference between a blood velocity measurement obtained before and after emitting an electrical pulse prior to ablation. The second change in blood velocity includes the difference between a blood velocity measurement obtained before and after emitting an electrical pulse subsequent to ablation. In some embodiments, the catheter further includes a blood velocity sensor. The electrical pulse emitted before ablation may have the same amplitude and duration as the electrical impulse emitted after ablation.

In some embodiments, the method further includes the steps of positioning the stimulation electrode against the wall of the artery at a second location, then measuring blood velocity, then emitting an electrical pulse, then measuring blood velocity again, and then ablating the artery wall at the second location.

In some embodiments, the method includes ablating nerves within an artery of a patient and includes advancing a catheter into the artery, the catheter comprising a first mapping electrode, a second mapping electrode, and an ablation element, wherein the ablation element may be one of the first or second mapping electrodes or may be a separate element. The method further includes positioning the first electrode against a wall of the artery at a first location and positioning the second electrode against the wall of the artery at a second location, then emitting a first electrical pulse from the first electrode, then detecting the first electrical pulse in the second electrode, wherein a characteristic of the detected pulse indicates conduction by a nerve, then ablating the artery wall at or near the first and/or second locations, and then during or after ablating, emitting a second electrical pulse from the first electrode at the first location and detecting the second electrical pulse in the second electrode at the second location.

In some embodiments, the step of emitting a second electrical pulse from the first electrode at the first location and detecting the second electrical pulse in the second electrode at the second location occurs during the step of ablating the renal artery wall. In some embodiments, the step of emitting a second electrical pulse from the first electrode and detecting the second electrical pulse in the second electrode includes continuously emitting electrical pulses from the first electrode at the first location and detecting the electrical pulses in the second location. In some such embodiments, the step of ablating the artery wall is stopped when a desired level of ablation is achieved as determined by the detected electrical pulses. In some such embodiments, the desired level of ablation may be less than complete ablation.

FIGURES

FIG. 3 is a diagram of a mapping and ablation catheter within the renal artery according to some embodiments;

FIG. 4 is a cross-section of a mapping and laser ablation catheter according to some embodiments;

FIG. 5 is a diagram of a mapping and laser ablation catheter being inserted into a renal artery according to some embodiments;

FIGS. 8A - 8C are a mapping and ablation catheter including a steerable guide catheter and a laser ablation catheter and cross-sectional views of each according to some embodiments;

DETAILED DESCRIPTION

Figure 1:
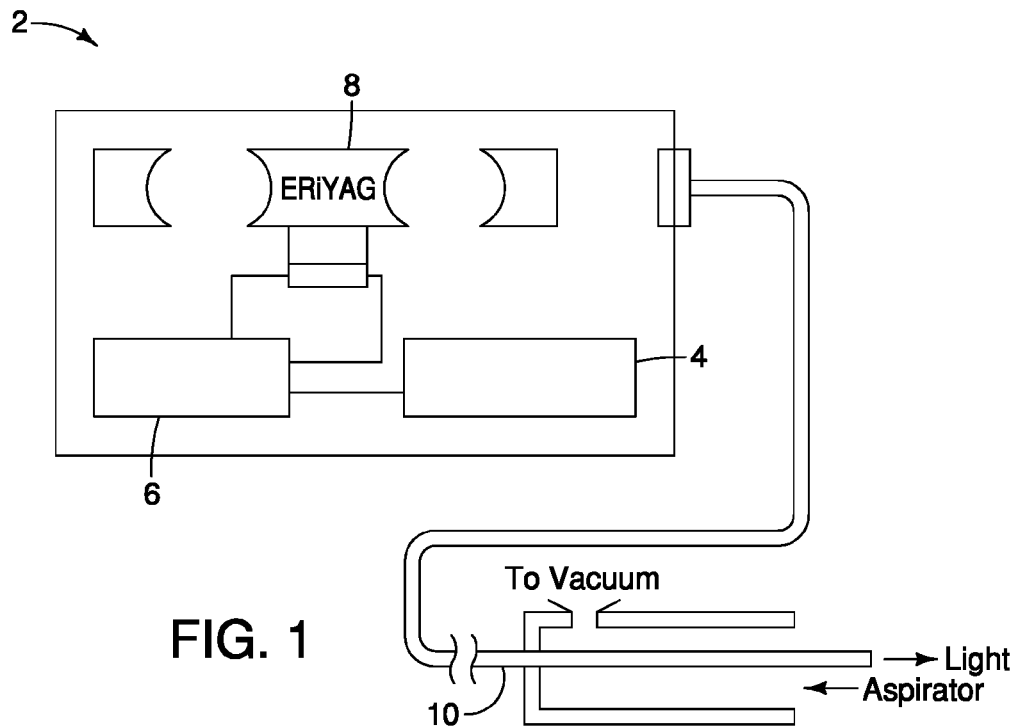
FIG. 1 is a schematic diagram of a system for nerve mapping and ablation according to various embodiments.

Embodiments of the invention selectively can localize and ablate nerves or nerve branches, such as the branches of the renal nerves within the renal arteries. By mapping the location of the branches of the nerves, the ablation can be performed through the tissue that overlies the nerve or nerve branch. The amount of ablation delivered to the tissue can, therefore, be reduced to only the amount necessary and not more, and the risk of side effects can also be reduced. In addition, when mapping is performed, by knowing the location of the nerve branches, the clinician can decide whether to ablate all or only some of the branches. If less than all of the branches of the nerve are ablated, some nerve function can be maintained, which may have some clinical benefits. For example, ablation of less than all of the sympathetic nerve branches in the renal artery may allow some sympathetic nerve stimulation of the kidney to be maintained, if desired. Furthermore, in some embodiments, the ablation may be performed using a non-electric modality such as laser, cryoablation, high frequency ultrasound, thermo ablation, or ablation by microwave energy, for example. In some such embodiments, the progress of nerve ablation can be monitored during ablation, such as monitoring changes in electrical conduction of the ablated nerve or changes in physiological parameters as described further below. The clinician can then determine when to stop ablation, which may be when the nerve is completely ablated or may be after only partial ablation of the nerve.

A branching system of nerves known as the renal plexus provides sympathetic stimulation to the kidneys. These nerves of the renal plexus extend to the kidneys by traveling within the walls of the renal arteries. The nerves divide into multiple branches as they extend distally within the walls of the renal arteries. Embodiments of the invention reduce or eliminate sympathetic stimulation to the kidneys by ablating some or all of these nerves. In some embodiments, the locations of one or more or all of the branches of these nerves are specifically identified within the walls of the renal arteries and ablation is then performed at these locations. As opposed to random or nonspecific ablation patterns, specific identification or mapping of the nerves reduces the amount of renal artery tissue which is ablated such that only the tissue at or around the nerve branches is ablated. This, in turn, may reduce the risk for long term complications such as renal artery stenosis and kidney failure. Specific site ablation may have similar benefits such as reduced stenosis when performed at other locations as well. Furthermore, specific mapping of each of the nerve branches allows a clinician to decide whether to ablate all or less than all of the branches. For example, it may be desirable to retain some amount of nerve stimulation and, therefore, a clinician may decide to ablate only a portion of the branches while leaving other branches intact without ablating them.

Embodiments of the invention identify the location of one or more nerves or nerve branches, such as the sympathetic nerve branches that travel within the walls of the renal arteries. In some embodiments, the locations of the nerve branches are identified by delivery of an electrical pulse at a first location and detection of the electrical pulse at a second location. The first and second locations may be endoluminal, within the arterial wall. In some embodiments, both the first and second locations are within a renal artery. The first location may be proximal (closer to the aorta) while the second location may be distal (such as closer to the kidney or other organ). In other embodiments, the first location is distal while the second location is proximal.

In some embodiments, the nerve mapping is performed endovascularly using a catheter. The catheter may include a first electrode for delivery of the electrical pulse at a first location and a second electrode for detection of the pulse at the second location. In embodiments in which the first pulse is delivered at a proximal location, the first electrode may be located proximally on the catheter and the second electrode may be located distally on or at the distal tip of the catheter. In embodiments in which the first pulse is delivered at a distal location, the first electrode may be located distally on the catheter or at the distal tip and the second electrode may be located proximally.

The catheter may be positioned such that the first and second electrodes abut or are in close proximity to the tissue, such as the inner surface of the renal artery, prior to delivery of the electrical pulse. Once so positioned, the electrical pulse may be delivered. If the second electrode detects conduction of the pulse consistent with conduction by a nerve, then it is known that a nerve branch is located at or near the location of each electrode. However, if conduction by a nerve is not detected, then the catheter may be repositioned such that the location of one or both of the electrodes is adjusted. This process may be repeated until the delivery of a pulse through a nerve is detected. When nerve conduction is detected, the location of the nerve within the tissue is identified as being directly or nearly directly beneath each of the first and second electrodes. As such, these electrodes perform a mapping function and may be described as mapping electrodes. Once the nerve location is identified, ablation may then be performed at either the first or second location or both. In some embodiments, ablation is performed using the same device as was used for mapping of the nerves. In some such embodiments, the ablation can be performed without moving the catheter. In other such embodiments, the catheter may be repositioned, such as by rotation and/or advancing or retracting the catheter to align the first and/or second locations with the ablation delivery mechanism. In some embodiments, the catheter is not repositioned at all or is only repositioned slightly for ablation, such that the mapping electrodes are still able to be used for detecting nerve conduction during the ablation procedure.

In some embodiments, the catheter used for nerve mapping may include more than two electrodes, such as three, four or more electrodes. In such embodiments, a first electrode may deliver an electrical pulse to the tissue and the second, third, and if present, additional electrodes may monitor second, third, and additional locations for conduction of the pulse by a nerve. In this way, multiple locations may be monitored for each pulse delivery.

When used in the renal artery and other locations having nerves or nerve branches of small size, it may be preferable to deliver nerve pulses having small amplitudes. For example, the energy pulse may have an amplitude of between about 0.1 mA and about 50 mA. The pulse rate may be between about 5 Hz and about 100 Hz. The pulse width may be between about 0.1 microseconds and about 100 microseconds. In some embodiments, a square pulse may be delivered, to be most clearly defined. In other embodiments, the pulse may be peaked or sinusoidal. The controller may detect conduction by a nerve branch by the characteristics of the detected signal and may use resistance to screen out background noise.

Ablation may be performed using any catheter based ablation delivery system. In some embodiments, RF energy is delivered to ablate the nerve branches identified by mapping as described herein. Devices which may be used for the ablation using RF energy may be unipolar or bipolar, such as ablation devices used for cardiovascular ablation. Such devices may be modified to include electrodes for detection of electrical conduction as described herein. Also, such devices may be used with an RF generator that is adjustable to achieve a desired Wattage that may be less than the Wattage used for cardiovascular ablation, such as about 2 Watts. In some embodiments, such RF ablation devices include at least a first and second electrode for identifying the locations of the nerve branches as well as one or more electrodes for delivering RF ablation energy. In such devices, the device may need to be adjusted (such as by rotating, advancing, or retracting) to align the ablative electrode with the nerve branch location after the location has been identified. Alternatively, if the detection electrode and the ablative electrode are in sufficiently close proximity on the device, such repositioning may not be required and ablation may be performed without repositioning the device. In other embodiments, the first and/or second mapping electrode may also function as an electrode for delivery of RF energy and/or as a return electrode for the RF energy. In such embodiments, one or both electrodes may function for both mapping of the nerve branch (by emitting or detecting a pulse) and for ablation (by RF energy delivery or return). In some embodiments, ablation is performed at a series of locations, with RF energy applied for about 2 minutes at about 8 Watts. The first location may be distally located within the renal artery, and each subsequent treatment location may be more proximally located than the previous locations and the device may be rotated to identify new locations as it is moved proximally. In addition, there may be a cooling period of about 5 minutes between ablations. A series of about 4 to about 6 ablations may be performed in some embodiments.

In other embodiments, the ablative energy is laser energy. In some such embodiments, the ablation device includes a YAG laser. Existing laser devices such as those used for cardiovascular procedures may be modified to include electrodes for detection of electrical conduction as described herein. In addition, the devices may need a power generator input with less input power than cardiovascular laser units and, therefore, a flexible power generator may be used. In some embodiments, the device includes an optical window through which the laser energy is delivered to the tissue. The device may also include a lens, radially inward from the optical window, or the window itself may also function as a lens. An optical window may be located directly adjacent to either the first or second electrode or both. In embodiments which include a third or additional electrodes for detection of an electrical pulse for localizing the nerve branches, an optical window may also be located directly adjacent to the third or additional electrodes. In such embodiments, energy can be selectively delivered through the optical window at a location corresponding to the identified location of the nerve branch, either without repositioning the catheter or with repositioning such as by rotating and/or advancing or retracting the catheter, depending upon the catheter design.

Other forms of ablation may alternatively be used, including cryoablation, high frequency ultrasound ablation (HIFU), microwave, thermoablation (heat) or other types of ablation as may be invented in the future, using any catheter based system known in the art or developed in the future. In each case, the ablation may be performed at a precise location in the tissue, such as through the wall of an artery such as the renal artery, to selectively ablate a nerve branch as described herein. For example, ablation systems that use electrical energy, such as RF, HIFU, microwave, and thermoablation, may be delivered using a flexible and/or extensible catheter. Non-electrical ablation systems, such as cryoablation, may be delivered using multiple electrodes on a balloon surface delivered by the catheter. Other non-electrical ablation systems, such as laser ablation, may include optic fibers and/or metal wires connected to electrodes. In some embodiments, the optic fiber may be coated with conductive metal.

The mapping and ablation catheter device may include a steerable guide catheter portion for navigating the catheter to the appropriate location, and a therapeutic catheter portion such as an ablation catheter portion which may include the mapping and ablation elements. The ablation catheter may reside within a lumen of the guide catheter and may include an ablation head that extends beyond the distal tip of the steerable guide catheter or may be extended upon demand by the clinician or other user. The ablation head may include the mapping and ablation elements and may also include ports for cooling solution entry and exit and temperature sensors. The mapping and ablation catheter may have an overall small diameter, such as about 6 French or less, making it easier to manipulate and position and making the use of the catheter less invasive. This small size may be achieved through the use of conductive optical fibers and reduced numbers of conductive wires or the elimination of conductive wires, such as in laser ablation systems. This small size allows precise ablation of the target tissue, with less damage to the surrounding tissue, reduced treatment time, access to smaller nerves particularly when used at other locations, less trauma, and faster patient recovery.

In some embodiments, the ablation catheter may include sensors for detecting a physiological parameter. For example, the ablation catheter may include a blood velocity sensor and/or a heart rate sensor. The sensors may be located on the distal tip or elsewhere on the ablation catheter. The sensors may be in communication with a control panel which can include a digital display of blood velocity, blood pressure, or other physiological parameter, such as by conductors running through a lumen in the ablation catheter.

In some embodiments, the steerable guide catheter may include a compound curvature that further assists in juxtaposing the ablation element against the target tissue. In some embodiments, only the distal end portion of the ablation catheter is movable, and the distal end portion may be able to move in multiple dimensional axis allowing the ablation catheter to be steered to the target site even in embodiments that do not include an additional guide catheter, even if the body of the ablation catheter is not steerable.

In some embodiments, some or all of the electrodes used for mapping and/or for ablation may be traditional conductive metal electrodes, for example. These electrodes may also be used for temperature monitoring during ablation, or other electrodes or sensors may be used.

In some embodiments, some or all of the electrodes may be printed screen electrodes on a surface, such as on an outer surface of the ablation catheter or on an expandable balloon. Such printed screen electrodes may include a printed electrode of a conductive material such as a conductive ink such as a platinum ink and printed conductors on a flexible film such as a polyimide film. The printed electrodes including the film may be applied directly to the surface and the printed conductors may attach proximally to a conductive wire. The printed electrodes can provide multiple data collection points to increase diagnostic and therapeutic capabilities and can reduce assembly complications while maintaining catheter flexibility, without increasing the catheter diameter.

In some embodiments, the progress of the ablation may be monitored by the system while the ablation is being performed such as by electrical monitoring of nerve conduction or of the response of a physiological parameter to nerve stimulation. In some such embodiments, the progress of the ablation may be continuously monitored as ablative energy is delivered. In other embodiments, the progress of the ablation may be intermittently monitored as ablative energy is delivered. In still other embodiments, the delivery of ablative energy may be momentarily halted to detect the progress of the ablation. For example, the delivery of ablative energy may be momentarily halted at periodic intervals at which time the progress of the ablation may be detected.

In some embodiments, the progress of ablation is detected by the delivery of a pulse of energy. The energy pulse may be delivered and detected using the same first and second (or third or additional) electrodes as were used to deliver the energy pulse for localization of the nerve or nerve branch that is being ablated. A single pulse of energy may be delivered or multiple pulses may be delivered at periodic intervals. For example, a series of pulses of energy may be delivered on a periodic basis as ablation is being performed. For example, pulses of energy may be delivered between about every 0.1 second and about every 5 seconds. In other embodiments, the pulses of energy may be delivered between about every 1 second and about every 5 seconds.

In some embodiments, the energy pulses delivered for ablation monitoring may be identical to the pulses delivered during localization in that they have the same frequency, amplitude, and duration, and may also be delivered identically throughout monitoring. In this way, changes in the characteristic of the energy pulse may be detected as ablation proceeds. Such changes may then be interpreted to correspond to the effectiveness or amount of ablation of the nerve branch achieved. For example, the changes in the electrical pulse that may correspond to the effectiveness of the ablation may be a decreased amplitude and/or a time delay (a shifting of the position of the waveform) from the original baseline amplitude and conduction time. Other changes which may be detected include tissue resistivity changes and delays in the signal responses at the receiving electrode due to a change in the pathway as the resistance of the nerve increases and the signal follows a new lower resistance pathway, such as through a different nerve or nerve branch.

In some embodiments, the progress of ablation may be monitored by monitoring physiological parameters in the tissue such as in an artery such as the renal artery, in an organ such as the kidney or elsewhere in the patient's body. Such parameters may include one or more of blood pressure, blood velocity, vessel diameter, vascular resistance, urine production rate, urinary sodium excretion rate, urinary potassium excretion rate, renin production, and/or renin excretion rate. Other physiological parameters that respond to partial and/or complete loss of nerve function such as sympathetic nerve stimulation of the kidneys may be used.

In some embodiments, the physiological parameter may be measured at the location of the ablation such as within an artery such as within the renal artery, and may be done by using the same catheter as was used for nerve localization and/or ablation. Alternatively, a separate catheter or separate measuring method may be used. In embodiments in which measurements are made in the urine, a urinary catheter may be used in the bladder, for example. In embodiments in which heart rate is measured, an EKG or other cardiac monitor may be used, for example. In some embodiments, blood pressure, blood velocity, diameter, and/or vascular resistance may be measured within an artery such as the renal artery using one or more sensors, such as a pressure sensor, flow sensor, ultrasonic sensor, or other known sensor technologies, which may or may not be a component of the mapping and/or ablation catheter. The physiological parameter may be one that is locally affected by nerve stimulation, rather than depending upon a system effect. For example, stimulation of the nerve may affect the physiological parameter at the level of the nerve location, such as the vessel, or the organ supplied by the vessel. An example of a physiological parameter which is affected locally by stimulation is blood velocity. While not intending to be bound by theory, it is believed that nerve stimulation in an artery such as the renal artery causes the release of epinephrine which leads to vasoconstriction and decreased blood velocity. Because this effect from nerve stimulation is rapid and direct, it makes a good response for monitoring for ablation. In contrast, parameters which change in response to nerve stimulation as a result of systemic effects, such as changes in heart rate, may be less useful as the result of the ablation is less direct and the parameter may be affected by other systemic factors as well.

Measurements of the physiological parameter may be made in order to determine the effectiveness of the ablation (the amount of denervation achieved). For example, a baseline measurement of the physiological parameter may be made prior to ablation. Ablation may then be performed. The physiological measurement may then be repeated, possibly after waiting a certain time period after the ablation. The amount of change in the physiological parameter (if any) may then be used to determine whether the desired degree of denervation has been achieved and whether or not an additional course of ablative energy should be delivered to the nerve. If additional ablation is performed, the physiological parameter can then be measured again and the process may be repeated until the change in the physiological parameter indicates that the desired amount of denervation has been achieved.

Alternatively, the effect of the nerve stimulation upon the physiological parameter may be used to assess the effectiveness of the ablation. In such embodiments, a baseline measurement of the physiological parameter may be obtained with and without stimulation of a renal nerve prior to ablation. Ablation of the nerve may then be performed. The physiological measurements may then be repeated, possibly after a time delay, both with and without stimulation of the ablated nerve. The amount of change in the physiological parameter due to nerve stimulation may change (decrease) as nerve conduction is decreased due to ablation and may be finally eliminated by ablation. One or more ablation steps may, therefore, be performed, followed by measurements of the physiological parameter with and without stimulation of the ablated nerve, until the desired amount of denervation has been achieved. That the desired amount of denervation has been achieved may be determined by observing that the amount of change of the physiological parameter caused by stimulation has changed (typically a decreased change) by the desired amount.

In each of the above examples, the amount of change in a physiological parameter, or the amount of change in the effect of stimulation on a physiological parameter, may be correlated to the amount of denervation (effectiveness of ablation) experimentally. For example, the parameters and/or the changes in the parameters due to stimulation may be correlated to the amount of denervation as determined by the measurements of both the parameters or changes in the parameters due to stimulation as well as electrical conduction in a number of individuals before and after ablation. Alternatively, the amount of ablation may be determined by correlating the parameter or change in the parameters due to stimulation to surgical findings for a group of individuals. This data may then be used to correlate the measurements of physiological parameters, or the changes in the parameters due to stimulation, in patients undergoing ablation to the amount of denervation achieved.

In some embodiments, the physiological parameter, or the change in the physiological parameter due to stimulation, may be measured before and after ablation. The measurement after ablation may be immediately after cessation of ablation or may be after a delay period. In some embodiments, the physiological parameter, or the change in the parameter due to stimulation, may be measured during ablation as a way to monitor the progress of the ablation. In some embodiments, the physiological parameter, or the change in the physiological parameter due to stimulation, may be measured before, during and after ablation. The measurement of the physiological parameter, or the change in the physiological parameter due to stimulation, may supplement the measurement of the nerve conduction as an additional way of monitoring the effectiveness of the ablation. If both nerve conduction and one or more physiological parameter or change in the physiological parameter are used to assess the progress of ablation, they may both be performed simultaneously, or they may be performed separately.

In another alternative, nerves may be stimulated using a pharmaceutical agent rather than electrical stimulation, and the physiological agent's effects may be measured as described above. For example, the sympathetic nerves of the renal artery may be stimulated using a pharmaceutical agent. The pharmaceutical agent may be delivered to the location such as the renal artery by the mapping and/or ablation catheter, for example. The effectiveness of the ablation may be monitored as described above by evaluating the response of the physiological parameter to chemical stimulation rather than electrical stimulation. One example of an appropriate pharmaceutical is norepinephrine, but other agents such as agents that stimulate nerves may alternatively be used.

In some embodiments, the clinician performing the ablation may elect to only partially ablate one or more of the nerve branches. In such embodiments, the clinician may elect to deliver ablative energy until ablation is partially complete as determined by monitoring the ablation progress as described herein. For example, the clinician may decide to ablate a nerve branch by a certain amount, and this amount may be determined by the amount of decrease in the measured amplitude of the signal, by the amount of time delay in transmission of the signal, by the change in a physiological parameter, and/or by the change in the effect of nerve stimulation on the physiological parameter.

The clinician may then deliver the ablative energy to the nerve while continuously or intermittently monitoring the progress of the ablation. When the monitoring shows that the desired amount of ablation has been achieved, the clinician may stop delivery of the ablative energy.

In some embodiments, the clinician may desire to completely ablate the nerve branch but may still monitor the progress of nerve ablation during the delivery of ablative energy. The clinician may continue delivery of the ablation energy until it is determined that no nerve conduction is occurring, such as by an absence of detectable nerve delivery of the energy pulse, or by the measurement of the physiological parameter or the effect of nerve stimulation on the physiological parameter. The clinician may then discontinue delivery of the ablative energy. In some embodiments, the clinician may continue delivery of some additional amount of energy after complete ablation is detected to provide a margin of error or to allow for some nerve recovery in the future. However, in either case, by monitoring the progress of the ablation, the clinician can determine when to stop ablation (whether immediately or after a certain amount of time after completion of ablation). As such, by monitoring completeness of ablation, the clinician can be assured that the ablation procedure was successful, since the monitoring shows that nerve conduction is no longer occurring.

In addition to assuring that ablation has occurred as planned, the use of monitoring during the ablation procedure can allow the clinician to use less ablative energy even when complete ablation is desired. The amount of energy needed to ablate a nerve branch at a location, such as within a renal artery, may vary among individuals, and could depend upon factors such as the size, age, gender, health status, or unique anatomy of the individual. In addition, even for an individual, the amount of energy needed to ablate a nerve branch may vary among the branches, depending, for example, upon the size of the branch or the depth of the branch within the tissue or the renal artery wall. Therefore, if the progress of the ablation is not monitored, a clinician would need to deliver the maximum amount of energy which might be necessary to every nerve branch and every individual to assure complete ablation of each nerve branch. This amount may be far greater than is actually needed. By monitoring the progress of the ablation, only the necessary amount of ablation needs to be delivered for each particular nerve branch and for each individual because the effectiveness of the ablation can be observed. In this way, by monitoring the progress of the ablation, the delivery of unnecessary amounts of ablative energy beyond what is needed for ablation can be avoided. It is anticipated that by reducing the amount of ablative energy delivered to the tissue, less damage is caused to the tissue such as the renal artery wall and, therefore, the risk of complications such as stenosis are further reduced.

In some embodiments, the mapping and ablation device includes one or more temperature sensors to detect the temperature of the tissue at or near the ablation site. In some embodiments, the temperature sensors may be electrodes such as metal electrodes which may include MEMS technology to convert the temperature to an output voltage. In some embodiments, the temperature may be measured using fiber optics, by sending and receiving a laser energy to detect changes in the radiance of the tissue relating to temperature, such as through non-touch thermal sensors. The temperature of the target tissue may be monitored during the ablation process to prevent damage to the tissue or to the blood, such as blood coagulation. For example, ablation may be stopped or decreased if the temperature of the tissue reaches between about 72° F. and about 75° F. or more, for example.

The use of ablation of the sympathetic nerves in the renal artery may be used to treat hypertension, such as hypertension which is resistant to drug treatment. However, other diseases that are thought to be caused by, or exacerbated by, sympathetic stimulation of the kidneys may also be treated by ablation of the sympathetic nerve branches in the renal arteries. Such diseases include chronic kidney disease, heart failure, and metabolic syndrome, for example.

It should further be noted that various embodiments of the invention may also be used for nerve localization followed by ablation and/or for monitoring of the progress of nerve ablation in other body locations. For example, selective nerve ablation may be used for the management of chronic pain, heart failure, and body weight, as well as the treatment of heart failure, diabetes (types 1 and 2), and atrial fibrillation. For example, chronic pain may be treated by ablation of the spinal cord, nerve roots, nerve bundles, nerves or nerve branches in locations where inflammation is causing pain. Heart failure and atrial fibrillation may be treated by epicardial ablation of nerves within the heart tissue, for example.

An example of a process for mapping and ablating a nerve within a tissue such as the wall of the renal artery will now be described. A catheter or other ablation device, such as a catheter having two-ring electrodes and a flow sensor, may be introduced into a patient and advanced to the treatment location, such as through the arterial system into the lumen of the renal artery. Normal blood velocity in the artery such as the renal artery may be measured to determine a baseline. The electrodes may be brought into proximity with the treatment location such as the artery wall and stimulation may be applied by one electrode. The ablation device may be repositioned and this process may be repeated until the stimulation is detected by the other electrode in an indication that electrical conduction has occurred through a nerve and that a nerve has, therefore, been located. A baseline measurement of a physiological parameter such as blood velocity may be obtained. A stimulation pulse may then be delivered to the nerve, and the measurement of the physiological parameter may then be repeated. For example, a square wave stimulation pulse may be delivered having an amplitude of about 40 volts, a width of 3 milliseconds, and a frequency of 5 cycles/second. A reduction in blood velocity of about 25 to 100% may occur. The change in blood velocity may be measured during nerve stimulation, immediately after nerve stimulation, or after some time delay. The measurement of a baseline physiological parameter and the physiological parameter during or after stimulation of the nerve may be repeated one or more times, such as after a delay or rest period, for verification. Ablation of the nerve may then be performed, at or essentially at the same location as the stimulation, using the same electrode as used for mapping and stimulation, or using a separate electrode or method. Following ablation, the same stimulation process as performed before ablation may be repeated by delivering an identical stimulation pulse, and the physiological parameter may be measured again in the same manner in which the baseline measurement was obtained. (A new baseline measurement may be obtained first, after ablation but prior to stimulation of the nerve. Alternatively, the original baseline measurement may be used.) The difference in the change in the physiological parameter caused by stimulation of the nerve, before as compared to after ablation, may then be calculated. If the difference correlates to adequate ablation, the process may be stopped. However, if the difference is not sufficient/too small, the steps of ablating and measuring the physiological parameter before and during or after stimulation may be repeated until the difference in change in the physiological parameter is sufficient to indicate that the desired amount of denervation has been achieved.

Figure 2:
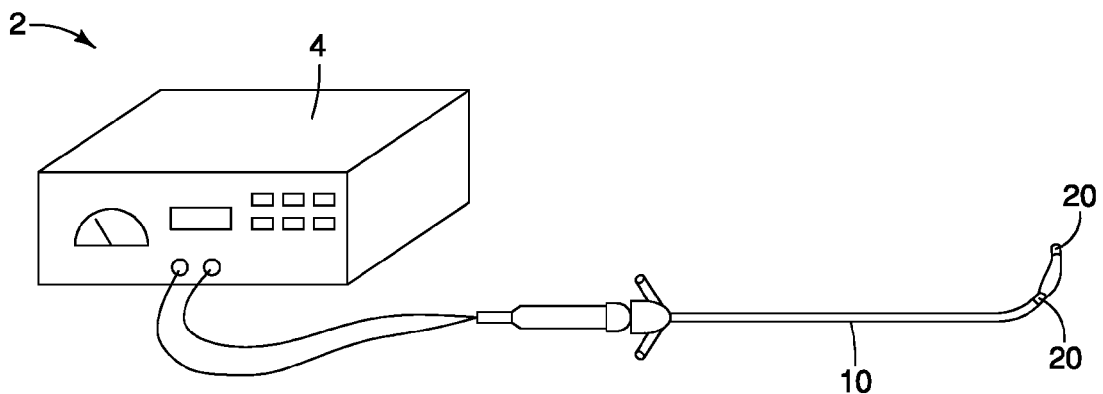
FIG. 2 is a diagram of a system for nerve mapping and ablation according to various embodiments.

An example of nerve mapping and ablation system that may be used on nerves in the renal artery is shown in FIG. 1. In this embodiment, the system delivers laser energy for ablation, but other forms of ablative energy could alternatively be used. The system 2 includes a controller 4 coupled to a power supply 6. A laser energy source 8, which in this example is an Erbium doped solid state gain medium, may have first and/or second resonant cavities and first and/or second couplers. The system further includes a catheter 10 for treatment delivery. An alternative example of a system 2 is shown in FIG. 2, which depicts a controller 4 connected to a steerable ablation catheter 10. Electrodes 20 are shown on the distal end of the catheter 10. In some embodiments of this catheter 10 as well as the others described herein, the catheter 10 may also include one or more sensors for measuring one or more physiological parameters at the treatment location such as within the renal artery.

FIG. 3 depicts a catheter 10 including an ablation catheter 12 surrounding a steerable guide catheter 14. The ablation catheter 12 includes electrodes 20 and an ablation head 22. The catheter 10 has been advanced through the aorta and into the renal artery.

FIGS. 4-7 depict laser energy catheters as examples of catheters which may be used in various embodiments. In FIG. 4, the catheter 10 includes a tip electrode 22 and ring electrodes 24. An optic window 30 located proximal to the tip electrode 22 allows laser energy to be directed out of the catheter and into the adjacent tissue. The catheter 10 also includes temperature sensors windows 40, or in other embodiments may include electrodes, for monitoring tissue temperature during laser ablation. Metal coated optic fibers 50 are shown delivering energy to the tip electrode 22, ring electrodes 24 and temperature sensors, but other conductors may alternatively be used.

Figure 6:
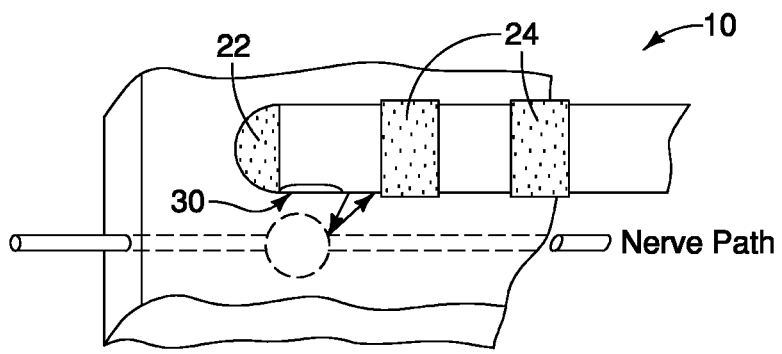
FIG. 6 is a diagram of a distal end of a mapping and ablation catheter within a renal artery according to some embodiments.
Figure 7:
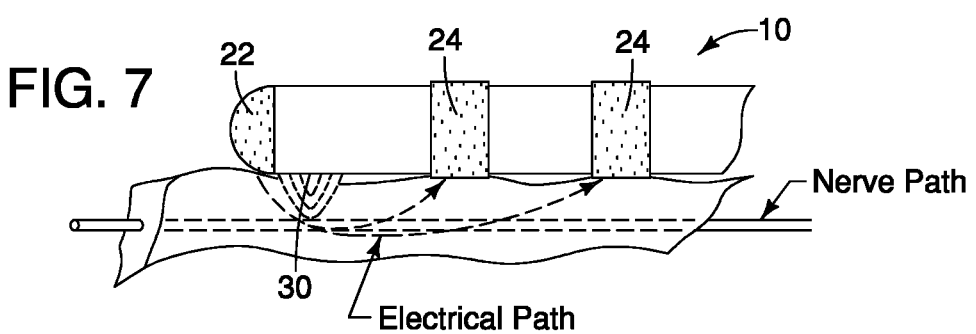
FIG. 7 is a diagram of a distal end of a mapping and ablation catheter delivering ablative energy to tissue and monitoring nerve conduction according to some embodiments.

In FIGS. 5 and 6, the laser energy catheter 10 is shown advancing into position in an artery. In FIG. 6, the laser window 30 is aligned with the identified ablation target tissue site at the nerve to transect the nerve's pathway. In FIG. 7, the catheter 10 can be seen simultaneously delivering laser energy through the laser window 30 into the tissue at the nerve location while monitoring the progress of ablation. In this example, the tip electrode 22 delivers energy into the tissue which is conducted by the nerve and detected by the ring electrodes 24.

FIG. 8A shows a side view of a laser energy catheter 10 which may be used in various embodiments. The catheter 10 includes electrodes 20, and an optic window 30. The laser ablation catheter 12 extends within the steerable guide catheter 14, though other configurations may alternatively be used. The cross section A-A in FIG. 8B shows a steering wire 54 for steering the catheter as well as a conductor 56 for supplying and/or receiving energy from the electrodes 20. The cross section at B-B shown in FIG. 8C shows the optic windows 30, a lens 32 located radially inward from the optic window 30, and an optic fiber 34 for delivery of the laser energy. In some embodiments, the ablation head 22 may be rotated with respect to the steerable guide catheter 14 so that the ablation head 22 is oriented toward the target tissue, regardless of the orientation of the steerable guide catheter 14. The proximal end of the steerable guide catheter (not shown) may be connected to a hub assembly including ports for cooling solution entry and exit, electrical connections, an optical connection to the laser source, and the necessary controlling mechanisms for steering and controlling the steerable guide catheter 14.

Figure 9:
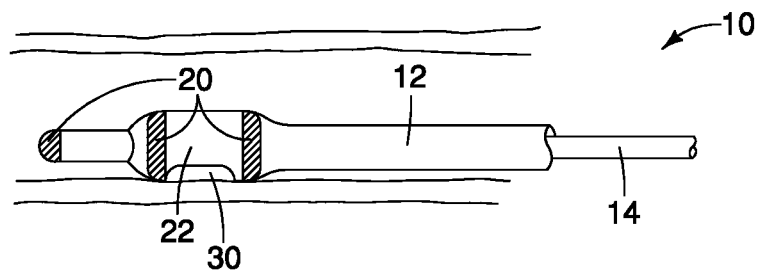
FIG. 9 is a diagram of a distal end of a mapping and ablation catheter according to some embodiments.

A further embodiment is shown in FIG. 9. The catheter 10 includes a steerable guidewire catheter 14 and a laser ablation catheter 12 which may be trackable surrounding the guidewire catheter 14. The optic window 30, electrodes 20, and ablation head 22 are also shown, and the catheter 10 is positioned within the artery.

Figure 10:
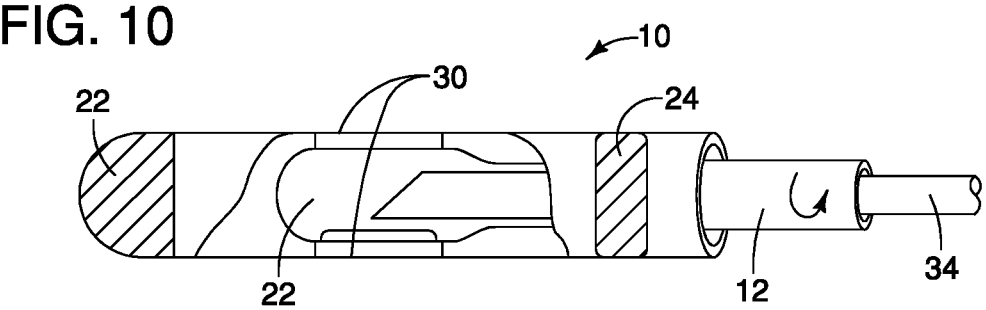
FIG. 10 is a diagram of a distal end of a mapping and ablation catheter according to some embodiments.
Figure 11:
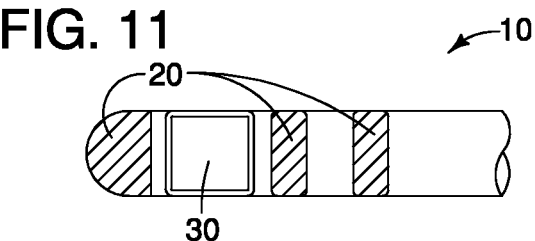
FIG. 11 is a diagram of a distal end of a mapping and ablation catheter having a cylindrical optic window according to some embodiments.
Figure 12:
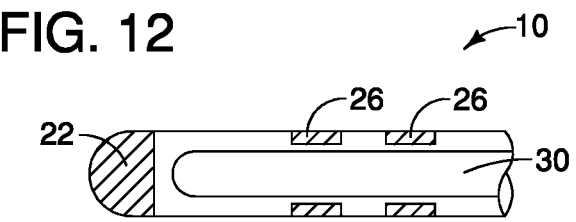
FIG. 12 is a diagram of a distal end of a mapping and ablation catheter having an elongated optic window according to some embodiments.
Figure 13:
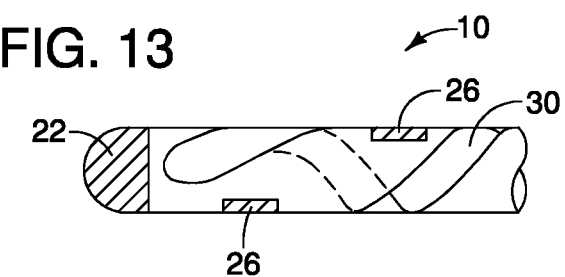
FIG. 13 is a diagram of a distal end of a mapping and ablation catheter having a coil shaped optic window according to some embodiments.
Figure 16:
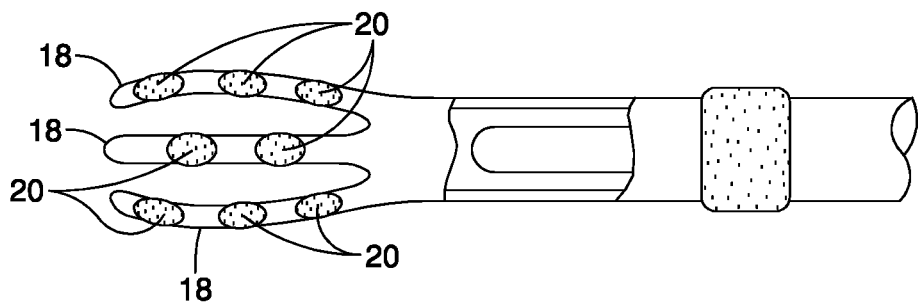
FIG. 16 is a diagram of a distal end of a mapping and ablation catheter having multiple distal tips according to some embodiments.

Various other alternative embodiments of the catheter 10 are shown in FIGS. 10, 11, 12, and 13. In FIG. 10, the laser ablation catheter 12 is rotatable and surrounds the optic fiber 34. In FIGS. 10 and 11, the optic window is cylindrical and extends around the circumference of the catheter 10. The rotatable laser ablation catheter 12 can be rotated to deliver laser energy through the optic window 30 in any direction without moving the tip electrode 22, such as while generating energy from tip electrode 22. In FIG. 12, the laser window 30 is rectangular, extending proximally/longitudinally past the electrodes 26 such that electrodes 26 are not ring electrodes in that they cannot encircle the catheter 10. Similarly, electrodes 26 in FIG. 16 are not ring electrodes because the coil shaped laser window 30 extends proximally past their locations. In these embodiments, the laser ablation catheter 12 can similarly be moved within the ablation head to deliver laser energy through a portion of the laser window to the identified target.

Figure 14:
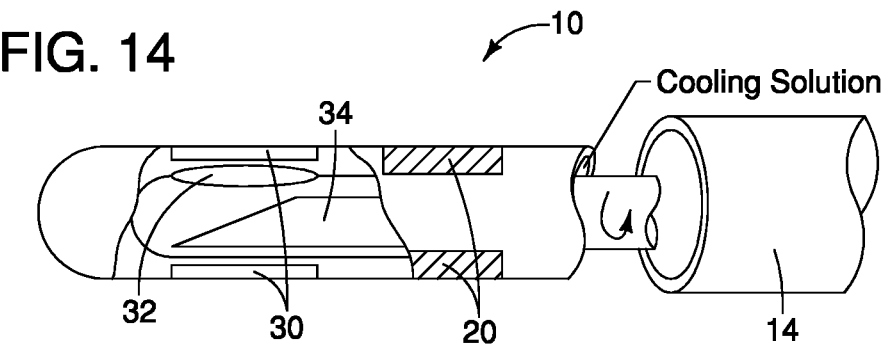
FIG. 14 is a cross sectional and exploded diagram of a distal end of a mapping and ablation catheter according to some embodiments.

Another embodiment is shown in FIG. 14. The rotatable optic fiber 34 can deliver laser energy through lens 32 and optic window 30. In this embodiment, a cooling solution may optimally be delivered through the catheter. The steerable guide catheter 14 is also shown.

Figure 15:
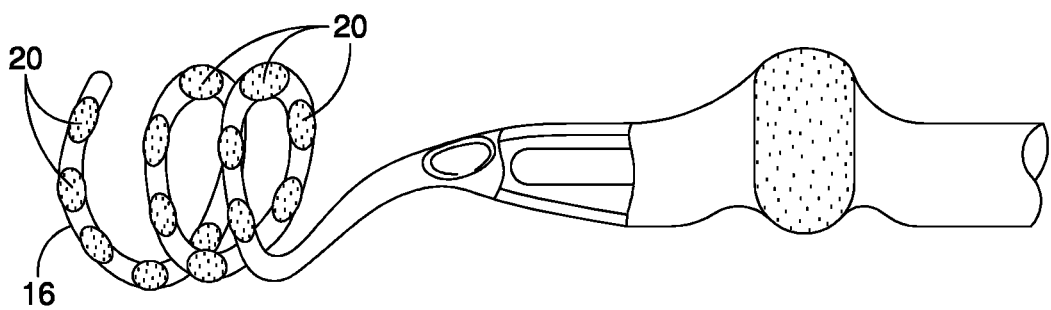
FIG. 15 is a diagram of a distal end of a mapping and ablation catheter having a coiled distal end according to some embodiments.

Other catheter shapes and configurations are also contemplated. For example, alternative electrode configurations are shown in FIGS. 15 and 16. In FIG. 15, numerous electrodes are located on the spiral shaped distal end 16 of the catheter 16. The catheter distal end spiral may be sized to abut the inner surface of the renal artery throughout its loops to allow for mapping around the artery without, or with less, repositioning of the catheter. In FIG. 16, the same objective can be achieved by splitting the distal end of the catheter into multiple ends 18 (in this case three) which extend distally and flare radially outward slightly, with electrodes 20 residing along the outer surface of each of these ends.

Figure 17:
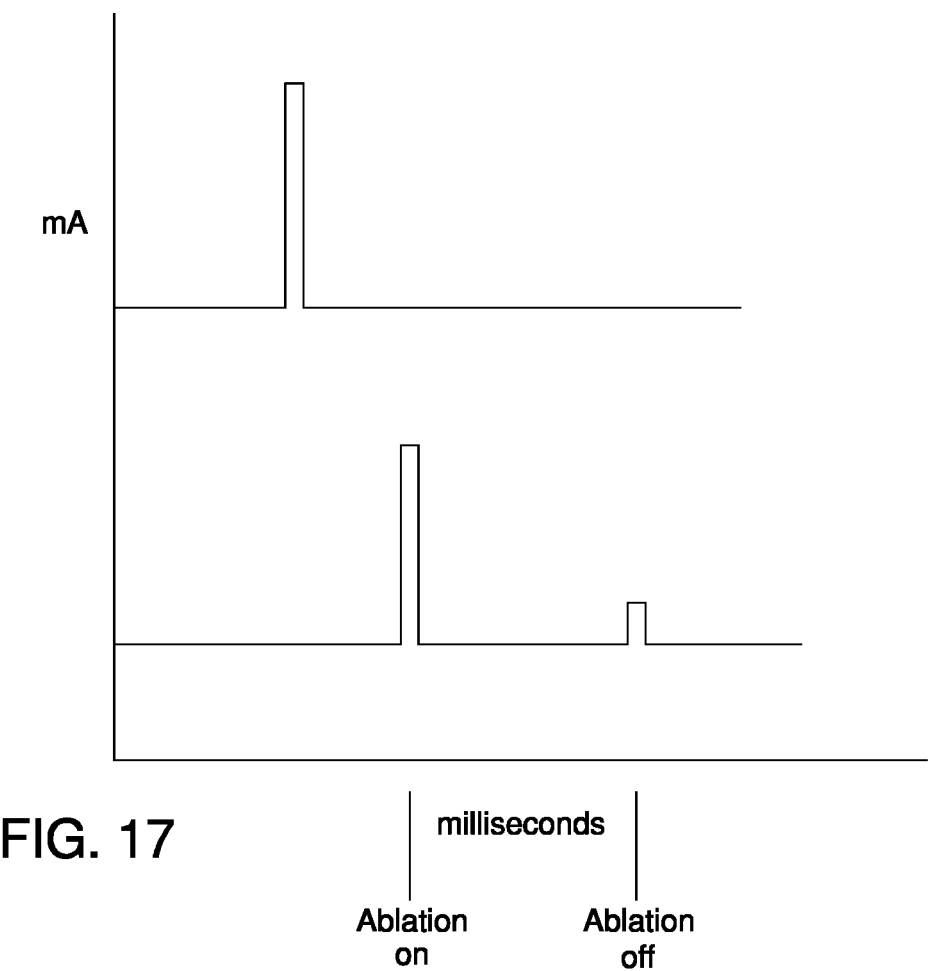
FIG. 17 is a graph of a nerve conduction signal according to some embodiments.

FIG. 17 shows a predictive example of an electrical signal being monitored during nerve ablation to monitor the effect of the ablation upon the nerve. In this particular example, the predicted response is shown for a square wave of energy delivered at an amplitude of 20 mA, a pulse rate of 50 Hz and a pulse width of 0.5 microsecond. The graph depicts mA verses time (milliseconds), with t0 being the time that the signal was delivered. By Ohm's law (V=IR), the tissue resistivity increases or/and the electrical pathway changes to a lower resistance pathway to delay detection of the signal. In FIG. 17, the upper graph depicts a baseline electrical pulse, prior to ablation. In comparison, the lower graph depicts changes due to ablation. The signal of the left side of the lower graph depicts an example of a change in amplitude and delayed conduction due to changes in resistivity of the conductive nerve pathway due to partial ablation. The signal on the right side of the lower graph depicts a signal which may be detected when the ablation is complete or nearly complete, with a greater decrease in amplitude and a greater delay in conduction. In some embodiments, the previous signal may be shown on the screen along with the current signal in order to aid in comparing and observing changes in the signal.

Figure 18:
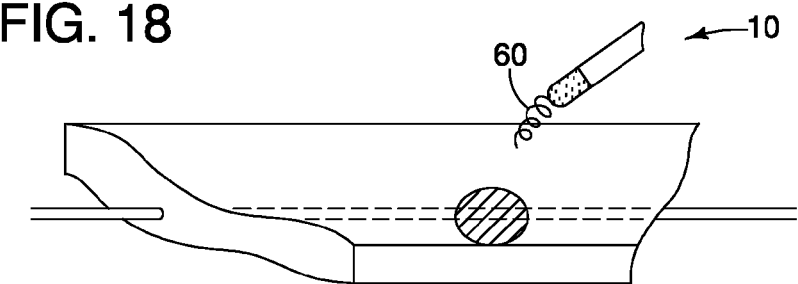
FIG. 18 is a diagram of a stimulator lead at a target site according to some embodiments.

In FIG. 18, a catheter 10 is shown in use according to alternative embodiments. In this alternative, the catheter 10 includes a spiral tip 60 which is a stimulation electrode. Alternatively, the spiral tip 60 may be drug coated for drug delivery to a target tissue site.

Figure 19:
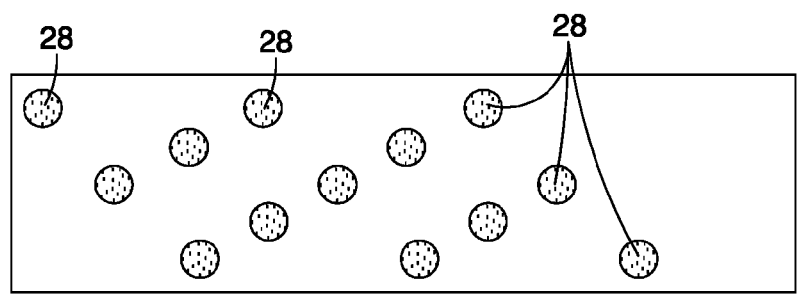
FIG. 19 and 20 are front and back views of printed electrodes according to some embodiments.
Figure 20:
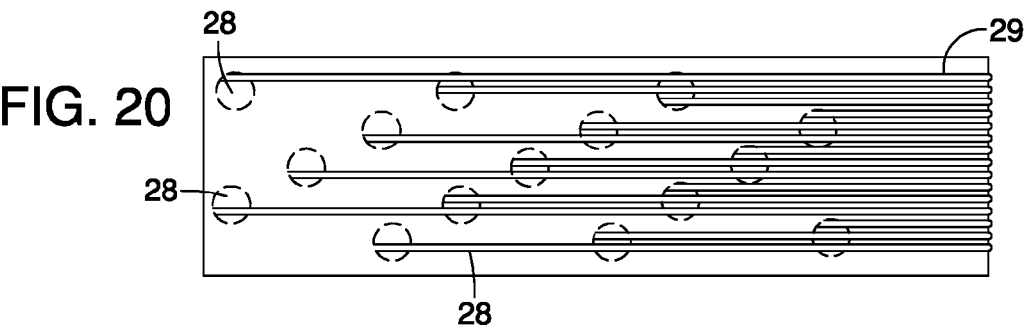
Figure 21:
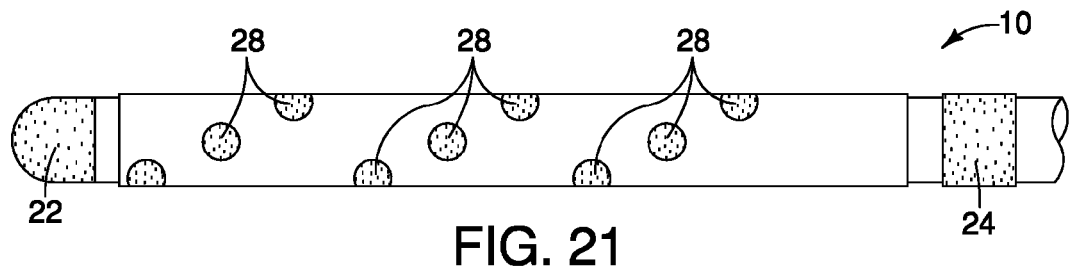
FIG. 21 is a mapping and ablation catheter including printed electrodes according to some embodiments.
Figure 22:
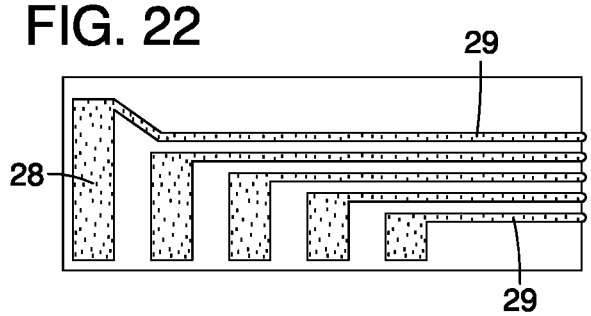
FIG. 22 is a front view of printed electrodes according to some embodiments.
Figure 23:
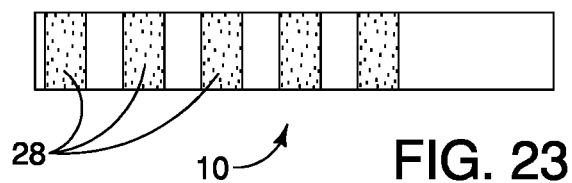
FIG. 23 is a diagram of a distal end of a mapping and ablation catheter including printed electrodes according to some embodiments.
Figure 24:
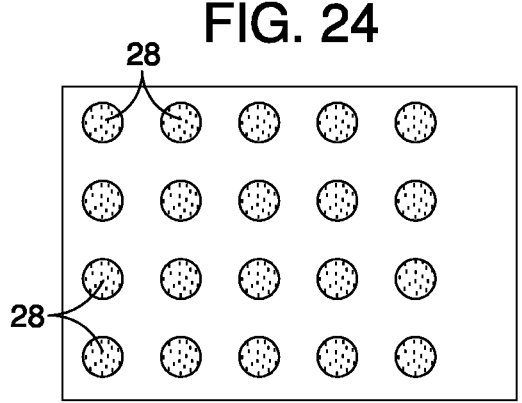
FIG. 24 and 25 are front and back views of printed electrodes according to some embodiments.
Figure 25:
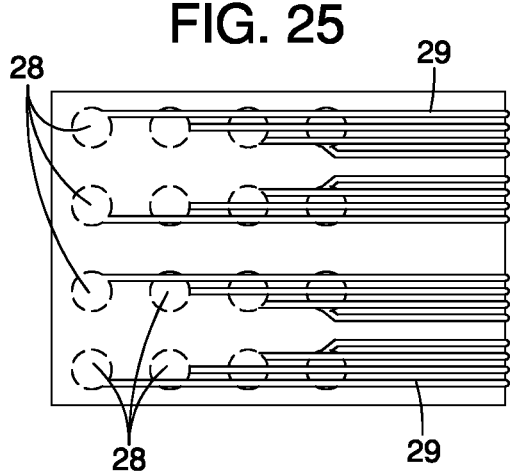
Figure 26:
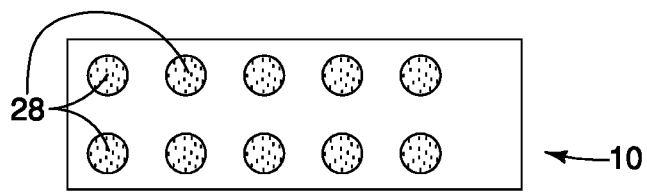
FIG. 26 is a diagram of a portion of a distal end of a mapping and ablation catheter including printed electrodes according to some embodiments.

FIG. 19-26 show circular screen printed electrodes 28 that may be used in various embodiments. The screen printed electrodes 28 shown in FIGS. 19 and 20 (front and back sides, respectively) are wrapped over the ablation catheter 10 in FIG. 21 to create a spiral pattern of electrodes 28 on the outer surface of the catheter 10. Each electrode 28 is printed onto a flexible film and is individually connected to printed conductors 29. In FIG. 19 and 20, the circuits are printed backside of the flexible film. In FIG. 21, the electrodes 28 are shown completely wrapped around catheter body. FIG. 22, 24 and 25 show different electrode designs and numbers of the electrodes 28. The rectangular electrodes 28 shown in 22 are wrapped around the catheter 10 of FIG. 23,and the regularly spaced circular electrodes 28 of FIGS. 24 and 25 are wrapped around the catheter 10 of FIG. 27.

EXPERIMENTAL

The following experiments were conducted to observe the change in the response of a physiological parameter to nerve stimulation as a result of at least partial ablation of the nerves within the renal artery. In particular, the experiment was performed to observe the effect of ablation of the nerves in the renal artery on the response of renal arterial blood velocity to a stimulation voltage applied to the nerves within the renal artery.

Figure 27:
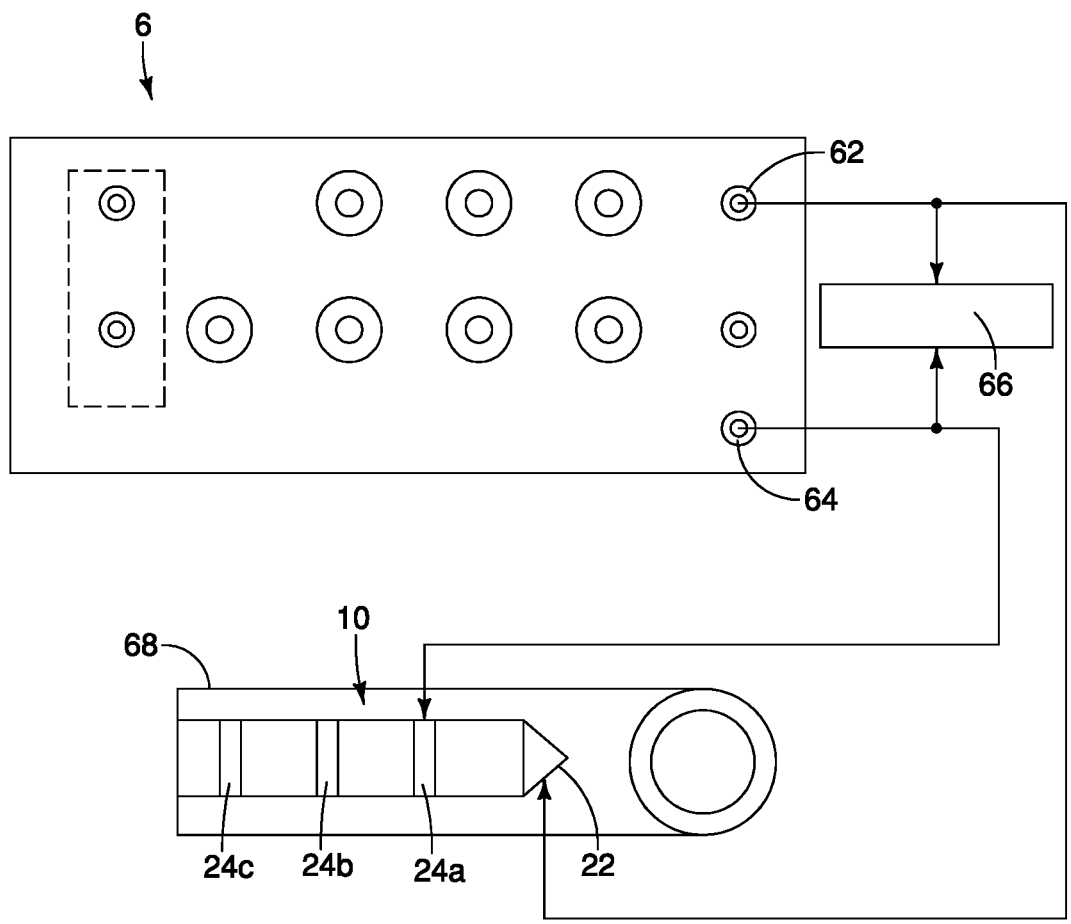
FIG. 27 is a schematic diagram of a mapping and ablation catheter and stimulation according to some embodiments.

A pig was sedated and a corkscrew RF energy ablation catheter comprising three ring electrodes and a tip electrode was inserted through the femoral artery and advanced into the right side renal artery. A schematic representation of the ablation catheter 10 including tip electrode 22, and first 24a, second 24b, and third ring electrodes 24c, and power supply 6 (stimulator) comprising an output terminal 62 and a ground terminal 64 is shown in FIG. 27. The signal from the power supply 6 may be monitored by a measuring device 66 such as oscilloscope. The catheter 10 of FIG. 27 is shown schematically as being located inside the renal artery 68. While FIG. 27 shows the first ring electrode 24a of the catheter 10 as the anode and the tip electrode 22 as the cathode, it will be appreciated that any one of the first 24a, second 24b, or third ring electrodes 24c as well as the tip electrode 22 may be either the cathode or the anode in various configurations, depending on which is electrically coupled to the output 62 and ground 64 terminals of the power supply 6, respectively. A scanning probe was also introduced and advanced intravenously to the right side renal artery to the location of the ablation catheter for measuring blood velocity. As the ablation catheter was repositioned at various times as described later in this section, the scanning probe was likewise repositioned next to the ablation catheter for measuring blood flow at each location.

Once in position in the artery, the resistances between the tip and the first ring electrode and between the tip and the third ring electrode were determined. This was performed by applying a voltage that measured 2.0 volts at open circuit across the electrodes and measuring the true voltage applied at the electrodes. The deviation of this voltage from the open circuit value of 2.0 volts is the amount of voltage dropped across the power supply's internal resistance, which was known to be about 240Ω. Thus, since a known voltage was dropped across a known resistance, the current flowing through the circuit was calculated using Ohm's Law. This current also flowed through the animal tissue, across which it was known that the remaining voltage was dropped. An additional application of Ohm's Law yielded the resistance value of the tissue between the voltage-supplying electrodes.

The determined tip-to-first ring and tip-to-third ring resistances were 666Ω and 903Ω, respectively.

Next, a series of electrical pulses of varying magnitude were applied between the tip and first ring electrodes of the ablation catheter, each contacting the inner wall of the right side renal artery. The electrical pulses were applied at a rate of 20 pulses per second, with a pulse width of 1 millisecond. The blood velocity through the renal artery was measured throughout the procedure using an ultrasound based scanning probe located next to the ablation catheter in the renal artery. After each stimulation pulse, the blood velocity was observed until the minimum blood velocity occurred, and the resultant decrease in blood velocity from the baseline to the minimum was noted. The change in blood velocity caused by each stimulation pulse is noted in Table 1 below.

Table 1 also shows the voltage applied by each stimulation pulse. It should be noted that, similarly to the resistance calculation described above, the true voltage delivered to the arterial tissue was different from the "open circuit" voltage that would have been present at the supply were there no load placed thereon due to the internal resistance of the power supply. This is because the arterial tissue provides a conduction path between the electrodes of the ablation catheter, allowing current to flow through the circuit and creating a voltage drop across the internal resistance of the supply. Therefore, for the purposes of clarity, both the open circuit and corresponding delivered voltages that were used are provided in Table 1 below, along with the observed change in renal artery blood velocity.

TABLE 1

Change in Renal Blood velocity at Various Voltages - Tip to First Ring

| Open Circuit Voltage | Delivered Voltage | Change in Renal Blood velocity |
|---|---|---|
| 10 | 6.0 | No Change |
| 20 | 11.5 | No Change |
| 30 | 16.4 | Small Change (not quantified) |
| 40 | 22.0 | Small Change (not quantified) |
| 52 | 27.2 | 10% Reduction |
| 60 | 31.2 | 20% Reduction |
| 70 | 37.6 | 40% Reduction* |
| 80 | 42.4 | 50% Reduction** |

Notes:
*Reduction took approximately 45 seconds to reach its minimum
**Reduction to minimum took much less time than the prior stimulation Select voltages were additionally applied between the tip and third ring electrodes at 20 pulses per second. Again, the change in blood velocity through the artery was measured in response to the voltage application. The results are summarized in Table 2 below:

TABLE 2

Change in Renal Blood velocity at Various Voltages - Tip to Third Ring

| Open Circuit Voltage | Delivered Voltage | Change in Renal Blood velocity |
|---|---|---|
| 60 | 35.2 | 10-15% Reduction |
| 80 | 45.6 | 40% Reduction |

It was observed that a greater voltage was required to effect the same change in blood velocity when compared to the closer spaced tip-to-first-ring trials. However, it was also observed that, with the increased separation of the electrodes, the reduction in blood velocity was effected more effectively on a voltage per distance between electrode [volts/mm] basis. That is, fewer volts/mm were required in the tip-to-third-electrode configuration to effect the same change in blood velocity when compared to the nearer tip-to-first-electrode configuration.

Once the baseline changes in the right renal artery blood velocity were obtained, an open circuit electrical stimulation pulse of 80 V was applied between the tip and first electrodes of the ablation catheter, resulting this time in a 40% reduction in renal blood velocity. Ablation was then performed between the electrode of the corkscrew ablation catheter and an animal grounding pad, wherein an ablation power of 15 W was applied for 60 seconds to the renal artery wall. After ablation, an open circuit electrical stimulation pulse of 80 V was once again applied to the electrodes of the ablation catheter, this time resulting in a 20% reduction in renal blood velocity. This decreased effect of the stimulation pulse on the renal artery blood velocity is indicative of the successful ablation of renal artery nerves.

Next, the ablation catheter and ultrasound probe were inserted into the left side renal artery for a similar procedure. A similar resistance measurement was conducted to determine the resistance of the tissue in a conduction path between various electrodes of the ablation catheter. The resistance between the tip and first ring electrode, and the resistance between the second and third ring electrodes were determined by the previously described process to be 588Ω and 1,115Ω, respectively. An 80-volt signal of 1 millisecond pulses at 20 Hz was applied between the second and third ring electrodes and effected a 40% reduction in blood velocity. Next, the ablation catheter was used to ablate the artery, applying 5 Watts between the tip electrode and an animal grounding pad for 60 seconds. The same 80-volt stimulation signal was applied between the second and third ring electrodes, and again effected a 40% reduction in blood velocity through the artery. With no change in the blood velocity reduction, the ablation was repeated using an increased power of 10 Watts for 60 seconds. In response, the artery spasmed down against the ablation catheter. Nitroglycerine was administered to reduce the spasm, but had no effect. The ablation catheter was withdrawn slightly, and another 80-volt stimulation signal was applied, though no blood velocity was measured. Additional attempts on the left side were abandoned due to the severe arterial spasm.

Approximately four hours after ablation was performed on the right renal artery, the ablation catheter and ultrasound probe were reinserted into the right side renal artery to test whether the effect of ablation on the change in renal artery blood velocity caused by a stimulation pulse was still present. An 80 V stimulation pulse was delivered identically to the pulses delivered previously, before and after ablation. The effect of the voltage on the renal blood velocity was a drop of almost 50%, which was similar to the effect seen previously, shortly following ablation. Thus, the observed effect of ablation on the voltage-induced reduction of blood velocity through the renal artery lasted at least throughout the duration of the experiment, and appears to be a viable metric for the degree and effectiveness of renal ablation.

The description provided herein is exemplary in nature and is not intended to limit the scope, applicability, or configuration of the invention in any way. Rather, the description provides practical illustrations for implementing various exemplary embodiments. Examples of constructions, materials, dimensions, and manufacturing processes are provided for selected elements, and all other elements employ that which is known to those of skill in the field.

Those skilled in the art will recognize that many of the examples provided have suitable alternatives that can be utilized.

The invention claimed is:

1. A method of ablating nerves within an artery of a patient comprising:
   a) advancing a catheter into the artery to a first location, the catheter comprising a first stimulation electrode and an ablation element;
   b) measuring a physiological parameter of the patient representing a progress of nerve ablation;
   c) after step b, emitting an electrical pulse from the first stimulation electrode into a wall of the artery at the first location;
   d) measuring the physiological parameter during or after step c);
   e) ablating the artery wall at the first location after step d);
   h) after step e), measuring the physiological parameter of the patient at the first location;
   i) after step h), emitting an electrical pulse from the first electrode at the first location;
   j) after step i), measuring the physiological parameter at the first electrode during or after step i);
   calculating a first change in the physiological parameter as a difference between a measurement obtained in step b) and a measurement obtained in step d), and calculating a second change in the physiological parameter as a difference between a measurement obtained in step h) and a measurement obtained in step j); and
   calculating a difference between the first change in the physiological parameter and the second change in the physiological parameter.

2. The method of claim 1 wherein the physiological parameter comprises blood velocity in the artery or artery diameter at the first location.

3. The method of claim 2 wherein the catheter further comprises a blood velocity sensor.

4. The method of claim 1 wherein the electrical pulse of step c) has an amplitude and duration equal to that of the electrical pulse of step i).

5. The method of claim 1 wherein if the difference between the first change in the physiological parameter and the second change in the physiological parameter is insufficient to indicate a desired amount of ablation, ablating the artery wall at the first location again.

6. The method of claim 1 further comprising, after performing steps a)-j):
   k) repositioning the catheter within the artery to a second location;
   l) after step k), emitting an electrical pulse from the first electrode at the second location;
   n) after step l), measuring the physiological parameter at the second location;
   o) after step n), ablating the artery wall at the second location.

7. The method of claim 6 further comprising measuring the physiological parameter at the second location between steps k) and l).

8. The method of claim 1 wherein the catheter further comprises a second stimulation electrode, the method further comprising, after performing steps a)-j):
   k) emitting an electrical pulse from the second stimulation electrode at a second location in the artery;
   l) after step k), measuring the physiological parameter at the second location,
   m) after step l), ablating the artery wall at the second location.

9. The method of claim 1 wherein the artery is a renal artery.

10. A method of ablating a nerve within an artery of a patient comprising:
    a) advancing a catheter into the artery, the catheter comprising a stimulation electrode and an ablation element, wherein the stimulation electrode and the ablation element may be one element or may be separate elements;
    b) positioning the stimulation electrode against a wall of the artery at a first location;
    c) measuring blood velocity in the artery at the first location;
    d) emitting an electrical pulse from the first electrode after step c);
    e) measuring blood velocity in the artery at the first location during or after step d);
    f) ablating the artery wall at the first location after step e);
    h) after step f), performing steps b), c), d) and e) a second time;
    i) if a difference between a first change in blood velocity and a second change in blood velocity is insufficient to indicate a desired amount of ablation, ablating the artery wall at the first location a second time;
    wherein the first change in blood velocity comprises a difference between a blood velocity measurement obtained in step c) and a blood velocity measurement obtained in step e) from the first time the blood velocity measurements in steps c) and e) were performed, and wherein the second change in blood velocity comprises a difference between a blood velocity measurement obtained in step c) and a blood velocity measurement obtained in step e) from the second time the blood velocity measurements in steps c) and e) were performed.

11. The method of claim 10 wherein the catheter further comprises a blood velocity sensor.

12. The method of claim 10 further comprising repeating steps b)-i) at a second location.

13. The method of claim 10 wherein the electrical pulse of step d) has an amplitude and duration equal when performed a first time as when performed a second time.

* * * * *